(12) United States Patent
Hazama

(10) Patent No.: US 7,006,925 B2
(45) Date of Patent: Feb. 28, 2006

(54) METHOD OF DETERMINING A BASE SEQUENCE FOR NUCLEIC ACID

(75) Inventor: Makoto Hazama, Hyogo (JP)

(73) Assignee: Shimadzu Corporation, Kyoto (JP)

( * ) Notice: Subject to any disclaimer, the term of this patent is extended or adjusted under 35 U.S.C. 154(b) by 388 days.

(21) Appl. No.: 10/003,120

(22) Filed: Dec. 6, 2001

(65) Prior Publication Data

US 2002/0090634 A1    Jul. 11, 2002

(30) Foreign Application Priority Data

Jan. 5, 2001    (JP)    ............................. 2001-000499

(51) Int. Cl.
*G06F 19/00*    (2006.01)

(52) U.S. Cl. .......................... 702/20; 702/19
(58) Field of Classification Search .................. 702/19, 702/20; 364/497; 435/6
See application file for complete search history.

(56) References Cited

U.S. PATENT DOCUMENTS 5,748,491 A  *  5/1998  Allison et al.  ................ 702/22

FOREIGN PATENT DOCUMENTS

JP    4-244953    9/1992

* cited by examiner

*Primary Examiner*—Ardin H. Marschel
*Assistant Examiner*—Jerry Lin
(74) *Attorney, Agent, or Firm*—Westerman, Hattori, Daniels & Adrian, LLP

(57) ABSTRACT

Waveform shaping by Fourier transformation is performed on data of N points from the head of detected data with a parameter of a previously set peak interval (S1, S2), base sequence is determined as to data of M points (M<N) from the head of the data of N points (S3), and a peak interval is obtained from the result of the sequence determination (S4). Waveform shaping by Fourier transformation is performed on data of N points from a position returning by L points (L<M) from final data of M points subjected to the sequence determination with a parameter of a precedently obtained peak interval, and thereafter the sequence determination, peak interval calculation and waveform shaping are similarly repeated. Thus, noise can be removed on the basis of Fourier transformation also as to a data section where a migration speed changes, for precisely determining the base sequence.

3 Claims, 2 Drawing Sheets ic acid on the basis of detected data, the data detected
METHOD OF DETERMINING A BASE SEQUENCE FOR NUCLEIC ACID

BACKGROUND OF THE INVENTION

1. Field of the Invention

The present invention relates to a method of sequence determination for nucleic acid such as DNA (deoxyribonucleic acid), and more particularly, it relates to a method of sequence determination for nucleic acid characterized in pretreatment carried out for removing noise before determining the base sequence from data obtained by electrophoresis.

2. Description of the Prior Art

In a method of electrophoresing a fragment sample of nucleic acid and determining the base sequence of the nucleby electrophoresis is a peak signal corresponding to the fragment samples of the nucleic acid. Since the peak signal includes noise components, waveform shaping is performed on the peak signal by pretreatment, for thereafter determining the base sequence on the basis of the peak signal.

The pretreatment is generally collectively performed on all detected data obtained by electrophoresis for thereafter performing a sequence determination (base calling) with treated waveforms.

The pretreatment for waveform shaping includes waveform shaping by Fourier transformation represented by FFT (fast Fourier transformation). In this pretreatment, filtering is performed when performing Fourier transformation on data of a peak signal detected by electrophoresis for thereafter returning the data to the peak signal by inverse Fourier transformation. A filter function employed in this filtering is adapted to remove signals having frequencies shorter than a DNA peak appearance interval, in order to mainly remove noise which is a high-frequency component.

① While FFT must be performed on $2^n$ data, the number of the data, varying with the migration time or the sampling frequency, is not constant.

② The filter function for noise removal is set for mainly removing noise which is a high-frequency component, i.e. a signal having a frequency shorter than the DNA peak appearance interval. Therefore, the migration speed serves as an important parameter for the filter function. However, the migration speed gradually changes during migration, and hence noise filtering cannot be performed with the same parameter over the overall data area.

SUMMARY OF THE INVENTION

Accordingly, an object of the present invention is to enable a precise sequence determination by removing noise also from a long data section, where a migration speed changes, on the basis of Fourier transformation.

A sequence determination according to the present invention shall be described with reference to FIG. 1.

The present invention is directed to a sequence determination for nucleic acid, electrophoresing a fragment sample of nucleic acid and determining the base sequence of the nucleic acid on the basis of detected data, comprising the following steps:

(A) a step (S1, S2) of performing waveform shaping by Fourier transformation on data of a certain number N of points from the head of the detected data with a parameter of a previously set peak interval;

(B) a step (S3) of determining the base sequence as to data of P points (P<N) from the head of the data of N points;

(C) a step (S4) of obtaining a peak interval from the result of the sequence determination;

(D) a step (S5, S6) of performing waveform shaping by Fourier transformation on data of N points from a position returning by L points (L<M) from final data precedently subjected to the sequence determination with a parameter of a precedently obtained peak interval; and (E) a step (S7) of determining the base sequence as to data of M points (M<N) of a central portion to be connected with data precedently subjected to the sequence determination among data of N points subjected to second or later waveform shaping.

The steps (E)→(C)→(D) are repeated until data disappear or no analysis is required despite presence of data due to attenuation of a signal or data abnormality.

The term "points" stands for data captured by performing scanning on set intervals in detection positions of electrophoresis, and the number of points corresponds to a migration time.

The Fourier transformation of the N point width and the sequence determination of the P or M point width included therein, which are completely independent processes with the parameter of the peak interval (migration speed), do not depend on the total data number.

The peak interval (migration speed) immediately preceding the Fourier transformation of the N point width is so utilized that appropriate parameters can be supplied to a filter function and the sequence determination, thereby improving precision of the sequence determination as a result.

According to the present invention, the waveform shaping by Fourier transformation is performed on the detected data of certain points with the parameter of the precedently obtained peak interval for determining the base sequence on the basis of the data subjected to the waveform shaping and progressing the treatment with partial overlapping of ranges subjected to the waveform shaping. In general, an analyzed (shaped) waveform after the sequence determination is also necessary for the sequence determination. While it is basically assumed that the analyzed waveform is discontinuous in the present invention, partial points are regularly subjected to Fourier transformation in an overlapped manner, whereby the analyzed waveform can be readily obtained by simply connecting sequence-determined portions.

When the overall data are collectively subjected to Fourier transformation, data of discontinuous portions appearing due to influence by bubbles or contaminants may exert bad influence on data of normal portions. According to the present invention, however, no influence is exerted before reaching a discontinuous portion.

Furthermore, the widths of the Fourier transformation and the sequence determination are fixed and independent of each other, whereby high flexibility is attained when adding a new rule or treatment.

The foregoing and other objects, features, aspects and advantages of the present invention will become more apparent from the following detailed description of the present invention when taken in conjunction with the accompanying drawing.

DESCRIPTION OF THE PREFERRED EMBODIMENTS

FFT treatment is applied as waveform shaping by Fourier transformation. In this case, the width (data number) of the FFT treatment is fixed to $2^n$ points for performing a sequence determination on central $2^{(n-1)}$ points after the treatment, obtaining a peak interval (migration speed) from the result of the sequence determination and performing the FFT treatment with the width of $2^n$ points again from a position of $2^{(n-1)}$ points of the rear half. This treatment is repeated up to the final data.

Figure 1:
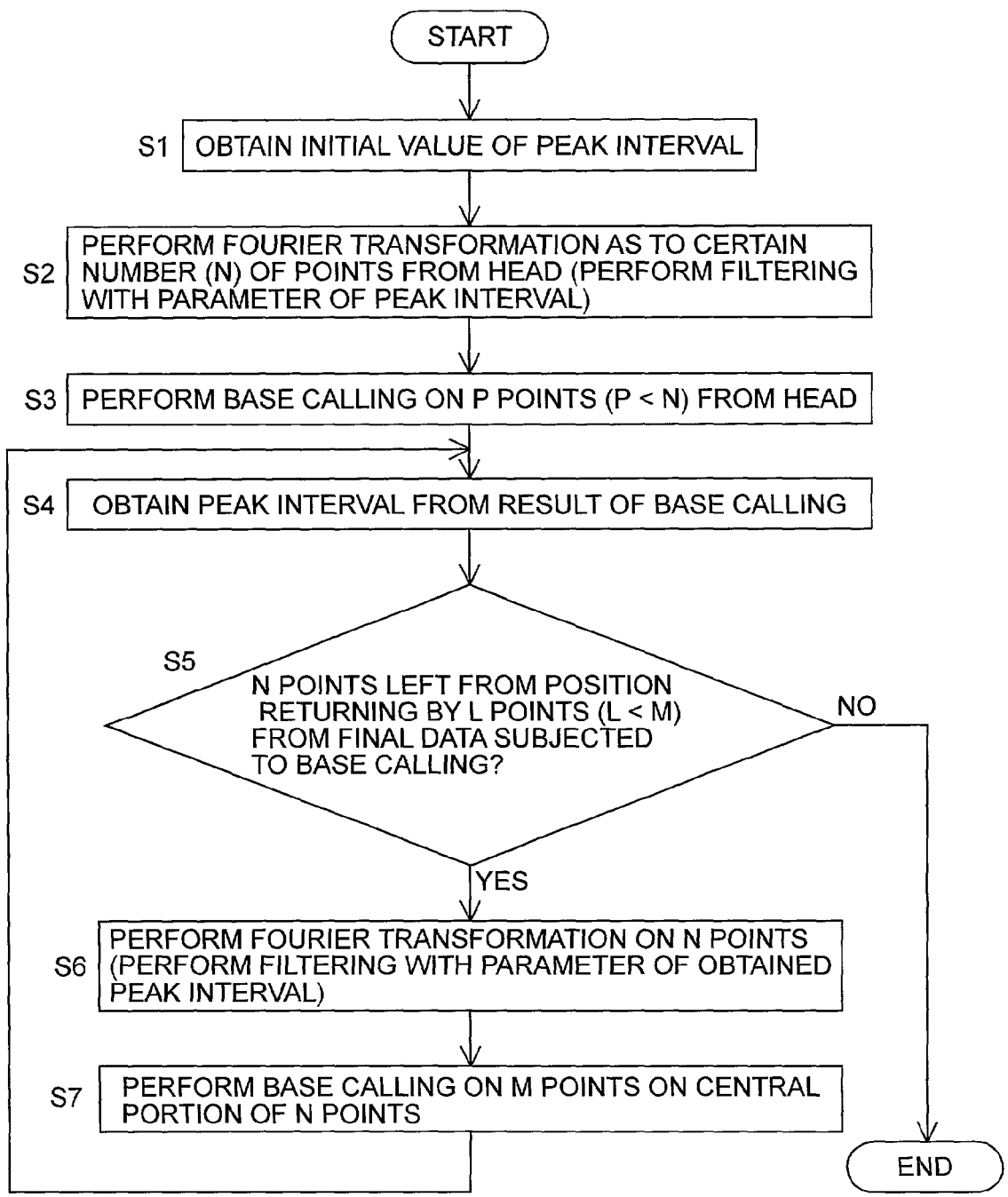
FIG. 1 is a flow chart illustrating the present invention.
Figure 2:
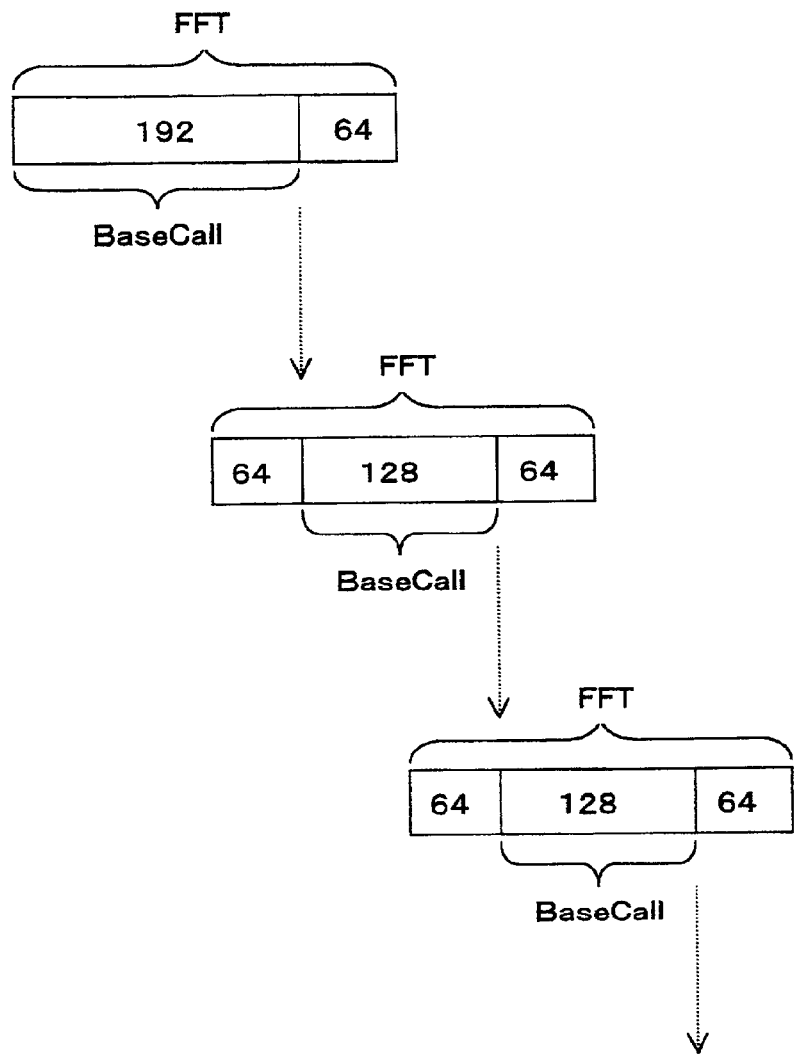
FIG. 2 schematically illustrates treatment according to an embodiment of the present invention.
Figure 3:
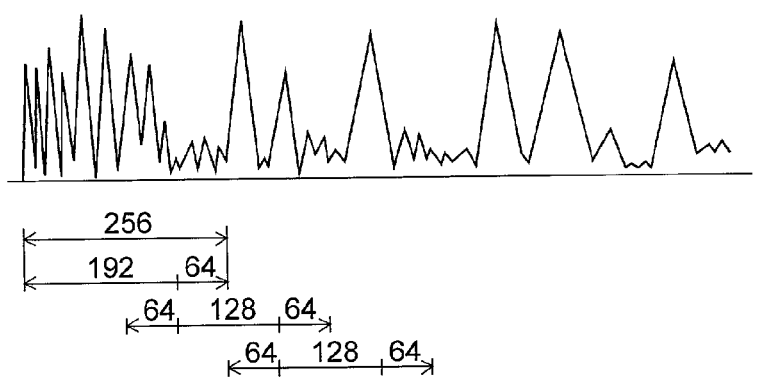
FIG. 3 illustrates the treatment according to the embodiment along with a waveform diagram showing a result of electrophoresis.

An embodiment of the present invention is described with reference to FIGS. 2 and 3.

According to the embodiment, FFT treatment is performed on $N=2^{(n=8)}=256$ points.

① An initial value of a peak interval is obtained. The initial value is previously set.

② FFT treatment is performed on N=256 points from the head. The FFT treatment is performed through a procedure of Fourier transformation→filtering with a parameter of the peak interval in the step ①→inverse Fourier transformation.

③ The sequence determination is performed as to P=192 points from the head with a parameter of the peak interval in the step ①.

④ The peak interval is obtained from the result of the sequence determination.

⑤ FFT treatment is performed on N=256 points from a position returning by L $(=2^{(n-2)})=64$ points from the back of the width employed for the sequence determination. The treatment is ended if there are no data of 256 points at this point in time. The FFT treatment is performed through a procedure of Fourier transformation→filtering with a parameter of the peak interval in the step ④→inverse Fourier transformation.

⑥ The sequence determination is performed as to M $(=2^{(n-1)})=128$ points from the head of L=64th point with a parameter of the peak interval in the step ④.

⑦ Return to the step ④.

While the width (data number) of the Fourier transformation is fixed to $2^n$ points in the embodiment due to the FFT treatment, the width N of Fourier transformation, the width P, M for the sequence determination and the width L for returning for the Fourier transformation are not limited to the numbers $2^x$ but may alternatively be integers satisfying relations N>M>L and N>P>L.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of data analysis for determining a base sequence for nucleic acid, based on detected data of electrophoresis of a fragment sample of nucleic acid, comprising steps of:
    (A) performing waveform shaping by Fourier transformation on data of a certain number N of points from the head of the detected data using a predetermined peak interval as a parameter;
    (B) determining the base sequence as to data of P points (P<N) from the head of the data of N points;
    (C) obtaining a subsequent peak interval from the result of the sequence determination in the most recent base sequence determination step;
    (D) performing waveform shaping by Fourier transformation on data of N points starting from a position returning by L points (L<M) from a final point of the data subjected to the sequence determination in the most recent base sequence determination step using the subsequent peak interval of the most recent step (C) as a parameter; and
    (E) determining the base sequence as to data of M points (M<N) of a central portion among the data of N points subjected to waveform shaping in step (D), so as to be connected with data most recently subjected to the sequence determination, wherein
    the steps (E)→(C)→(D) are repeated until all data has been analyzed or no analysis is required despite presence of data, and
    (F) determining a base sequence of nucleic acid by connecting sequence-analyzed portions.

2. The method of data analysis for determining a base sequence for nucleic acid according to claim 1, wherein
    fast Fourier transformation (FFT) treatment is applied to at least one of steps (A) or (D) as the waveform shaping by Fourier transformation.

3. The method of data analysis for determining a base sequence for nucleic acid according to claim 2, assuming that N is equal to $2^n$, M is equal to $2^{(n-1)}$ and L is equal to $2^{(n-2)}$, where n is an integer.

* * * * *